(12) United States Patent
Faram

(10) Patent No.: US 9,050,434 B2
(45) Date of Patent: Jun. 9, 2015

(54) LUNG THERAPY DEVICE

(75) Inventor: Joseph Dee Faram, Dallas, TX (US)

(73) Assignee: Comedica Incorporated, Dallas, TX (US)

( * ) Notice: Subject to any disclaimer, the term of this patent is extended or adjusted under 35 U.S.C. 154(b) by 1233 days.

(21) Appl. No.: 12/121,421

(22) Filed: May 15, 2008

(65) Prior Publication Data

US 2008/0283051 A1 Nov. 20, 2008

Related U.S. Application Data

(60) Provisional application No. 60/938,865, filed on May 18, 2007.

(51) Int. Cl.
| | | |
|---|---|---|
| *F16C 1/08* | (2006.01) | |
| *A61M 15/00* | (2006.01) | |
| *A61M 16/10* | (2006.01) | |
| *A61M 15/08* | (2006.01) | |
| *A61M 16/08* | (2006.01) | |
| *A61M 16/20* | (2006.01) | |
| *A61M 16/12* | (2006.01) | |
| *A61M 11/02* | (2006.01) | |
| *A61M 16/14* | (2006.01) | |
| *A61M 16/00* | (2006.01) | |

(52) U.S. Cl.
CPC ........... *A61M 16/0875* (2013.01); *A61M 11/02* (2013.01); *A61M 15/0028* (2013.01); *A61M 16/14* (2013.01); *A61M 16/20* (2013.01); *A61M 2016/0027* (2013.01); *A61M 2205/582* (2013.01); *A61M 2205/583* (2013.01); *A61M 16/127* (2014.02); *A61M 16/201* (2014.02)

(58) Field of Classification Search
USPC ............ 128/203.12, 200.11–200.24, 203.15, 128/203.23, 204.14
See application file for complete search history.

(56) References Cited

U.S. PATENT DOCUMENTS

| | | | |
|---|---|---|---|
| 402,779 | A | 5/1889 | Steinhoff |
| 1,150,238 | A | 8/1915 | Winbray |
| 3,068,856 | A | 12/1962 | Bird et al. |
| 3,083,707 | A | 4/1963 | Seeler |
| 3,291,122 | A | 12/1966 | Engstrom et al. |
| 3,301,255 | A | 1/1967 | Thompson |
| 3,537,448 | A | 11/1970 | Liston |
| 3,561,444 | A | 2/1971 | Boucher |
| 3,584,621 | A | 6/1971 | Bird et al. |
| 3,630,196 | A | 12/1971 | Bird et al. |
| 3,664,337 | A | 5/1972 | Lindsey et al. |

(Continued)

OTHER PUBLICATIONS

A Manual on VDR-Volumetric Diffusive Repiration (VDR)—The VDR-4 Percussionator for the Most Challenging Patients Requiring Mechanical Cardiopulmonary Care—Percussionaire Corporation, Idaho, Copyright 1996 (75 pages).

(Continued)

*Primary Examiner* — Kristen Matter
(74) *Attorney, Agent, or Firm* — Hitchcock Evert LLP

(57) ABSTRACT

The invention relates in general to a respiratory therapy device, and more specifically to an apparatus and method for providing continuous positive airway pressure therapy that may be connected to a small-volume nebulizer in order to provide a combination therapy that requires only a single source of gas. The apparatus of the invention includes a valveless patient interface and a source of pressurized gas which may be split into two streams to provide both continuous positive airway pressure therapy as well as aerosol therapy to a patient.

16 Claims, 2 Drawing Sheets

(56) References Cited

U.S. PATENT DOCUMENTS

| | | |
|---|---|---|
| 3,861,386 A | 1/1975 | Harris et al. |
| 4,054,134 A | 10/1977 | Kritzer |
| 4,062,358 A | 12/1977 | Kritzer |
| 4,106,504 A * | 8/1978 | York ........................ 128/204.24 |
| 4,182,599 A | 1/1980 | Eyrick et al. |
| 4,195,044 A | 3/1980 | Miller |
| 4,245,633 A | 1/1981 | Erceg |
| 4,263,907 A | 4/1981 | Lindsey |
| 4,436,090 A | 3/1984 | Darling |
| 4,471,773 A | 9/1984 | Bunnell et al. |
| 4,558,710 A | 12/1985 | Eichler |
| 4,592,349 A | 6/1986 | Bird |
| 4,601,465 A | 7/1986 | Roy |
| 4,635,857 A | 1/1987 | Hughes |
| 4,747,402 A | 5/1988 | Reese et al. |
| 4,770,164 A | 9/1988 | Lach et al. |
| 4,805,613 A | 2/1989 | Bird |
| 4,823,784 A | 4/1989 | Bordoni et al. |
| 4,838,260 A | 6/1989 | Bird |
| 4,867,151 A | 9/1989 | Bird |
| 4,930,501 A | 6/1990 | Bird |
| 4,951,659 A | 8/1990 | Weiler et al. |
| 4,964,404 A | 10/1990 | Stone |
| 4,973,047 A | 11/1990 | Norell |
| 4,981,295 A | 1/1991 | Belman et al. |
| 5,007,420 A | 4/1991 | Bird |
| 5,018,517 A | 5/1991 | Liardet |
| 5,027,809 A | 7/1991 | Robinson |
| 5,067,707 A | 11/1991 | Kohnke |
| 5,069,449 A | 12/1991 | Wardwell |
| 5,107,830 A | 4/1992 | Younes |
| 5,116,088 A | 5/1992 | Bird |
| 5,127,400 A | 7/1992 | DeVries et al. |
| 5,150,291 A | 9/1992 | Cummings et al. |
| 5,165,398 A | 11/1992 | Bird |
| 5,193,529 A | 3/1993 | Labaere |
| 5,261,394 A | 11/1993 | Mulligan et al. |
| 5,277,175 A * | 1/1994 | Riggs et al. ............. 128/200.21 |
| 5,322,057 A | 6/1994 | Raabe et al. |
| 5,355,873 A | 10/1994 | Del Bon et al. |
| 5,390,665 A | 2/1995 | Leach |
| 5,398,676 A | 3/1995 | Press et al. |
| 5,413,110 A | 5/1995 | Cummings et al. |
| 5,415,161 A | 5/1995 | Ryder |
| 5,423,313 A | 6/1995 | Olsson et al. |
| 5,439,430 A | 8/1995 | Rubens et al. |
| 5,451,190 A | 9/1995 | Liardet |
| 5,479,920 A | 1/1996 | Piper et al. |
| 5,535,738 A | 7/1996 | Estes et al. |
| 5,542,416 A | 8/1996 | Chalvignac |
| 5,547,440 A | 8/1996 | Rubens et al. |
| 5,570,682 A | 11/1996 | Johnson |
| 5,586,551 A * | 12/1996 | Hilliard ................... 128/203.29 |
| 5,598,839 A | 2/1997 | Niles et al. |
| 5,617,844 A | 4/1997 | King |
| 5,617,847 A | 4/1997 | Howe |
| 5,664,562 A | 9/1997 | Bourdon |
| 5,666,945 A | 9/1997 | Davenport |
| 5,694,919 A | 12/1997 | Rubsamen et al. |
| 5,713,349 A | 2/1998 | Keaney |
| 5,823,179 A | 10/1998 | Grychowski et al. |
| 5,829,429 A | 11/1998 | Hughes |
| 5,862,802 A | 1/1999 | Bird |
| 5,906,198 A | 5/1999 | Flickinger |
| 5,937,857 A | 8/1999 | Caterini et al. |
| 5,938,117 A | 8/1999 | Ivri |
| 5,950,619 A | 9/1999 | Van Der Linden et al. |
| 5,964,223 A | 10/1999 | Baran |
| 5,970,974 A | 10/1999 | Van Der Linden et al. |
| 6,044,841 A | 4/2000 | Verdun et al. |
| 6,058,932 A | 5/2000 | Hughes |
| 6,076,519 A | 6/2000 | Johnson |
| 6,076,520 A | 6/2000 | Cooper |
| 6,079,413 A | 6/2000 | Baran |
| 6,085,740 A | 7/2000 | Ivri et al. |
| 6,085,746 A | 7/2000 | Fox |
| 6,116,233 A | 9/2000 | Denyer et al. |
| 6,167,881 B1 | 1/2001 | Hughes |
| 6,210,345 B1 | 4/2001 | Van Brunt |
| 6,234,167 B1 | 5/2001 | Cox et al. |
| 6,240,919 B1 | 6/2001 | MacDonald et al. |
| 6,269,810 B1 | 8/2001 | Brooker et al. |
| 6,289,892 B1 | 9/2001 | Faithfull et al. |
| 6,302,105 B1 | 10/2001 | Wickham et al. |
| 6,336,455 B1 | 1/2002 | Howlett |
| 6,340,025 B1 | 1/2002 | Van Brunt |
| 6,355,002 B1 | 3/2002 | Faram et al. |
| 6,363,932 B1 | 4/2002 | Forchione et al. |
| 6,402,046 B1 | 6/2002 | Loser |
| 6,405,934 B1 | 6/2002 | Hess et al. |
| 6,412,481 B1 | 7/2002 | Bienvenu et al. |
| 6,415,791 B1 | 7/2002 | Van Brunt |
| 6,425,393 B1 | 7/2002 | Lurie et al. |
| 6,427,690 B1 | 8/2002 | McCombs et al. |
| 6,435,175 B1 | 8/2002 | Stenzler |
| 6,450,163 B1 | 9/2002 | Blacker et al. |
| 6,467,476 B1 | 10/2002 | Ivri et al. |
| 6,526,976 B1 | 3/2003 | Baran |
| 6,540,153 B1 | 4/2003 | Ivri |
| 6,540,154 B1 | 4/2003 | Ivri et al. |
| 6,546,927 B2 | 4/2003 | Litherland et al. |
| 6,550,472 B2 | 4/2003 | Litherland et al. |
| 6,550,476 B1 | 4/2003 | Ryder |
| 6,557,549 B2 | 5/2003 | Schmidt et al. |
| 6,568,387 B2 | 5/2003 | Davenport et al. |
| 6,571,790 B1 | 6/2003 | Weinstein |
| 6,581,596 B1 | 6/2003 | Truitt et al. |
| 6,581,598 B1 | 6/2003 | Foran et al. |
| 6,581,600 B2 | 6/2003 | Bird |
| 6,588,421 B1 | 7/2003 | Diehl et al. |
| 6,588,422 B1 | 7/2003 | Berthon-Jones et al. |
| 6,595,203 B1 | 7/2003 | Bird |
| 6,598,602 B1 | 7/2003 | Sjoholm |
| 6,598,603 B1 | 7/2003 | Andersson et al. |
| 6,609,517 B1 | 8/2003 | Estes et al. |
| 6,612,303 B1 | 9/2003 | Grychowski et al. |
| 6,615,831 B1 | 9/2003 | Tuitt et al. |
| 6,626,175 B2 | 9/2003 | Jafari et al. |
| 6,631,721 B1 | 10/2003 | Salter et al. |
| 6,640,806 B2 | 11/2003 | Yurko |
| 6,644,304 B2 | 11/2003 | Grychowski et al. |
| 6,644,310 B1 | 11/2003 | Delache et al. |
| 6,644,311 B1 | 11/2003 | Truitt et al. |
| 6,663,574 B2 | 12/2003 | Faram et al. |
| 6,679,258 B1 | 1/2004 | Strom |
| 6,694,969 B1 | 2/2004 | Heinonen et al. |
| 6,702,998 B2 | 3/2004 | Conner |
| 6,708,688 B1 | 3/2004 | Rubin et al. |
| 6,718,969 B1 | 4/2004 | Rubin et al. |
| 6,722,362 B2 | 4/2004 | Hete et al. |
| 6,729,327 B2 | 5/2004 | McFarland, Jr. |
| 6,729,334 B1 | 5/2004 | Baran |
| 6,737,042 B2 | 5/2004 | Rabinowitz et al. |
| 6,752,151 B2 | 6/2004 | Hill |
| 6,776,159 B2 | 8/2004 | Pelerossi et al. |
| 6,805,118 B2 | 10/2004 | Brooker et al. |
| 6,805,120 B1 | 10/2004 | Jeffrey et al. |
| 6,823,866 B2 | 11/2004 | Jafari et al. |
| 6,848,443 B2 | 2/2005 | Schmidt et al. |
| 6,851,426 B1 | 2/2005 | Jaffre et al. |
| 6,854,462 B2 | 2/2005 | Berthon-Jones et al. |
| 6,880,556 B2 | 4/2005 | Uchiyama et al. |
| 6,904,906 B2 | 6/2005 | Salter et al. |
| 6,907,881 B2 | 6/2005 | Suki et al. |
| 6,910,479 B1 | 6/2005 | Van Brunt |
| 6,915,803 B2 | 7/2005 | Berthon-Jones et al. |
| 6,932,084 B2 | 8/2005 | Estes et al. |
| 6,948,497 B2 | 9/2005 | Zdrojkowski et al. |
| 6,968,840 B2 | 11/2005 | Smith et al. |
| 7,011,091 B2 | 3/2006 | Hill et al. |
| 7,013,894 B2 | 3/2006 | McFarland, Jr. |
| 7,036,500 B2 | 5/2006 | Niles et al. |
| 7,059,324 B2 | 6/2006 | Pelerossi et al. |
| 7,066,176 B2 | 6/2006 | Jaffe et al. |

(56) References Cited

U.S. PATENT DOCUMENTS

| | | | |
|---|---|---|---|
| 7,070,761 B2 | 7/2006 | Rabinowitz et al. | |
| 7,077,133 B2 | 7/2006 | Yagi et al. | |
| 7,100,607 B2 | 9/2006 | Zdrojkowski et al. | |
| 7,128,069 B2 | 10/2006 | Farrugia et al. | |
| 7,131,439 B2 | 11/2006 | Blacker et al. | |
| 7,165,547 B2 | 1/2007 | Truitt et al. | |
| 7,188,621 B2 | 3/2007 | DeVries et al. | |
| 7,191,776 B2 | 3/2007 | Niles et al. | |
| 7,191,780 B2 | 3/2007 | Faram | |
| 7,204,245 B2 | 4/2007 | Johnson et al. | |
| 7,210,480 B2 | 5/2007 | Lurie et al. | |
| 7,232,417 B2 | 6/2007 | Plante | |
| 7,302,949 B2 | 12/2007 | Pelerossi et al. | |
| 7,445,607 B2 | 11/2008 | Plante | |
| 7,469,700 B2 | 12/2008 | Baran | |
| 7,472,702 B2 | 1/2009 | Beck et al. | |
| 7,472,705 B2 | 1/2009 | Baran | |
| 7,500,481 B2 | 3/2009 | Delache et al. | |
| 7,562,657 B2 | 7/2009 | Blanch et al. | |
| 7,600,511 B2 | 10/2009 | Power et al. | |
| 7,699,054 B2 | 4/2010 | Pelerossi et al. | |
| 2003/0051731 A1 | 3/2003 | Be'eri et al. | |
| 2003/0140921 A1 | 7/2003 | Smith et al. | |
| 2003/0140925 A1 | 7/2003 | Sapienza et al. | |
| 2003/0145849 A1 | 8/2003 | Drinan et al. | |
| 2003/0183226 A1 | 10/2003 | Brand et al. | |
| 2003/0205229 A1 | 11/2003 | Crockford et al. | |
| 2004/0003814 A1* | 1/2004 | Banner et al. | 128/204.21 |
| 2005/0061318 A1* | 3/2005 | Faram | 128/204.18 |
| 2005/0109340 A1 | 5/2005 | Tehrani | |
| 2005/0150489 A1 | 7/2005 | Dunfield et al. | |
| 2005/0165334 A1 | 7/2005 | Lurie | |
| 2005/0172954 A1 | 8/2005 | Smith et al. | |
| 2005/0217666 A1 | 10/2005 | Fink et al. | |
| 2006/0144398 A1 | 7/2006 | Doshi et al. | |
| 2006/0178245 A1 | 8/2006 | Schiller et al. | |
| 2006/0201500 A1 | 9/2006 | Von Hollen et al. | |
| 2006/0243274 A1 | 11/2006 | Lieberman et al. | |
| 2006/0272642 A1 | 12/2006 | Chalvignac | |
| 2007/0017522 A1 | 1/2007 | Be-Eri et al. | |
| 2007/0017523 A1 | 1/2007 | Be-Eri et al. | |
| 2007/0089740 A1* | 4/2007 | Baumert et al. | 128/203.12 |
| 2007/0186928 A1 | 8/2007 | Be'Eri | |
| 2008/0000475 A1 | 1/2008 | Hill | |
| 2008/0000477 A1 | 1/2008 | Huster et al. | |
| 2008/0015456 A1 | 1/2008 | McCawley et al. | |
| 2008/0091117 A1 | 4/2008 | Choncholas et al. | |
| 2008/0190429 A1 | 8/2008 | Tatarek | |
| 2008/0264412 A1* | 10/2008 | Meyer et al. | 128/200.22 |
| 2008/0283060 A1 | 11/2008 | Bassin | |
| 2009/0020121 A1 | 1/2009 | Bassin | |

OTHER PUBLICATIONS

Bird Demand CPAP, Bird Technical Information Manual, Copyright 1977 Bird Corp. (138 pages).

The Percussionaire Gold Edition IPV-1S(r) Universal Percussionator—Form 33120 Percusionaire Corporation, Idaho (2 pages).

The Basic Institutional Intrapulmonary Percussionator—Percussionaire Model IPV-1—Percussionaire Corporation, Idaho (2 pages).

The Bird—Instructor Reference Manual by Forrest M. Bird for the Bird Institute of Respiratory Technology, Apr. 1976 (14 pages).

Organization and Set Up of the Percussive VDR Intensive Care Breathing Circuit VDR Failsafe Breathing Circuit for Intensive Care—Percussionaire Corporation, Idaho (31 pages).

Intrapulmonary Percussive Ventilation IPV Discussion paper, Copyright Percussionaire 2000 (30 pages).

Specifications for Spanker Respirators, Copyright Percussionaire 1985 (6 pages).

Percussionaire Product Sheet, Dec. 12, 2002 (2 pages).

IPV-1C Institutional Intrapulmonary Percussionator spec., by Percussionaire Oct. 28, 2001 (2 pages).

IPV Users Manual, Copyright Percussionaire Dec. 1, 2000 (48 pages).

Letter dated Nov. 12, 2009 with enclosed Response dated Feb. 6, 2009 (80 pages).

* cited by examiner

LUNG THERAPY DEVICE

CROSS-REFERENCE TO RELATED APPLICATION

This application claims the benefit of priority from U.S. Provisional Application No. 60/938,865 filed on May 18, 2007.

FIELD OF THE INVENTION

The invention relates in general to a respiratory therapy device, and more specifically to an apparatus and method for providing continuous positive airway pressure therapy that may be connected to a small-volume nebulizer in order to provide a combination therapy that requires only a single source of gas.

BACKGROUND OF THE INVENTION

The health field is replete with devices intended to help resolve or prevent respiratory problems. Therapies that assist persons in taking deep breaths have been found to be beneficial in that this may expand airways. Among these therapies are continuous positive airway pressure therapy, and aerosol therapy.

Continuous positive airway pressure therapy, or "CPAP," is often used for the treatment and prevention of atelectasis, which is the closing of part or the entire lung. Atelectasis is usually due to blockage in the airway and is exacerbated by very shallow breathing. CPAP is often used in hospitals on post surgical patients and patients who are confined to bed because they are particularly vulnerable to this condition. CPAP, which is also used to treat sleep apnea, delivers a positive pressure into the airways during both inhalation and exhalation in order to help open the airways and keep them open. It has been found to help in not only the reversal of atelectasis, but in its prevention as well. CPAP therapy may be delivered by connecting a single-patient CPAP device to a source of gas, such as a flow meter that regulates the flow of air or oxygen from a wall outlet. CPAP therapy is most often delivered to the patient through a mouthpiece or mask.

Another lung therapy that is commonly used to prevent or resolve atelectasis is aerosol therapy. This therapy is typically delivered by placing a liquid medication, such as a bronchodilator, into a small-volume nebulizer, connecting the nebulizer to a source of gas, most often regulated by a flow meter that regulates the flow of air or oxygen. The nebulizer converts the liquid medication into aerosol and, like CPAP therapy, is usually delivered to the patient through a mouthpiece or mask.

It has been found that the combination and concurrent delivery of CPAP and aerosol therapies is beneficial in that it reduces treatment time, and it is believed that each therapy enhances the effectiveness of the other. The aerosol delivery of a fast-acting bronchodilator may help to dilate airways allowing the CPAP pressure being introduced to have the maximum opportunity to be effective. Likewise, as the CPAP holds the airways open the aerosol has free access to the airways to do its job. This combination therapy may be administered by connecting a single-patient CPAP device to one source of gas controlled by a flow meter, connecting a nebulizer to the CPAP device, and connecting the nebulizer to another source of gas controlled by a flow meter.

Although this combination therapy is effective, potential problems may arise by having to connect each of the two therapy devices to separate gas sources. For example, there is often only one gas source available in a hospital room. In this case, a concurrent combination therapy would be precluded, or require the gathering of an additional portable gas source, such as a gas tank or portable compressor. If two gas sources are available in a room, an additional flow meter is required so that the nebulizer and the CPAP device can each be connected to its own gas source. Additionally, if there are two gas sources in a room, usually one is oxygen and the other air. This forces the clinician to connect one of the devices to air and the other to oxygen. In certain situations it may be advantageous to connect both the CPAP device and the nebulizer to the same type of gas. For example, in treating a patient in the end-stages of chronic obstructive pulmonary disease, it may be desirable to deliver the combination therapy using only air in order to avoid oxygen-flow induced retention of carbon dioxide. Similarly, when treating a patient with a condition that requires higher concentrations of oxygen it may be more beneficial to connect both the CPAP and the aerosol device to an oxygen source.

Thus, it would be desirable to have a single-patient, CPAP therapy device that can be connected to a nebulizer in order to deliver aerosol therapy under continuous positive pressure while requiring only a single gas source for the two devices or combination.

The present invention provides for such a combination therapy and connects to a single gas source.

SUMMARY OF THE INVENTION

The invention is a respiratory therapy device that provides continuous positive airway pressure and may be connected to a small-volume nebulizer to deliver a combination CPAP-aerosol therapy while connecting to a single gas source. It is comprised of a single-patient use continuous positive airway pressure therapy device, connectable to a small-volume nebulizer, a means for connecting both devices to a single gas source, and a means for restricting the flow of gas to at least one of the two devices.

Accordingly, an object of the present invention is to provide a means for delivering a CPAP-aerosol combination therapy even when only one gas source is available.

Another object of the present invention is to save time required in gathering additional gas sources and flow control devices in order to deliver a CPAP-aerosol combination therapy.

Another object of the present invention is to save the expense required securing additional gas sources and flow control devices in order to deliver a CPAP-aerosol combination therapy.

Another object of the present invention is to provide a means to connect both the CPAP device and the nebulizer to the same gas when only one air source and one oxygen source are available.

A BRIEF DESCRIPTION OF THE DRAWINGS

DETAILED DESCRIPTION

Figure 1:
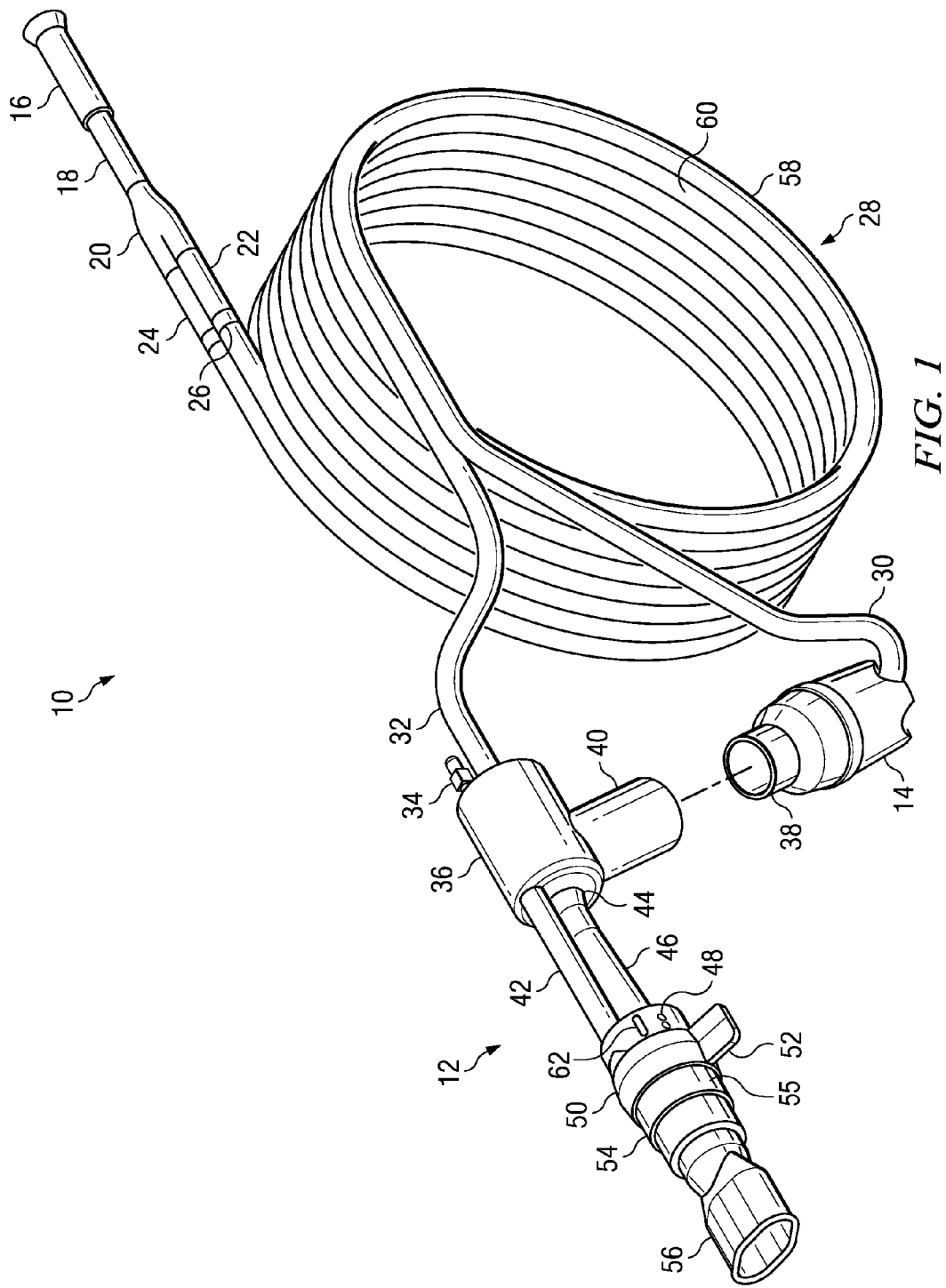
FIG. 1 is a view of a preferred embodiment of the lung therapy device of present invention.
Figure 2:
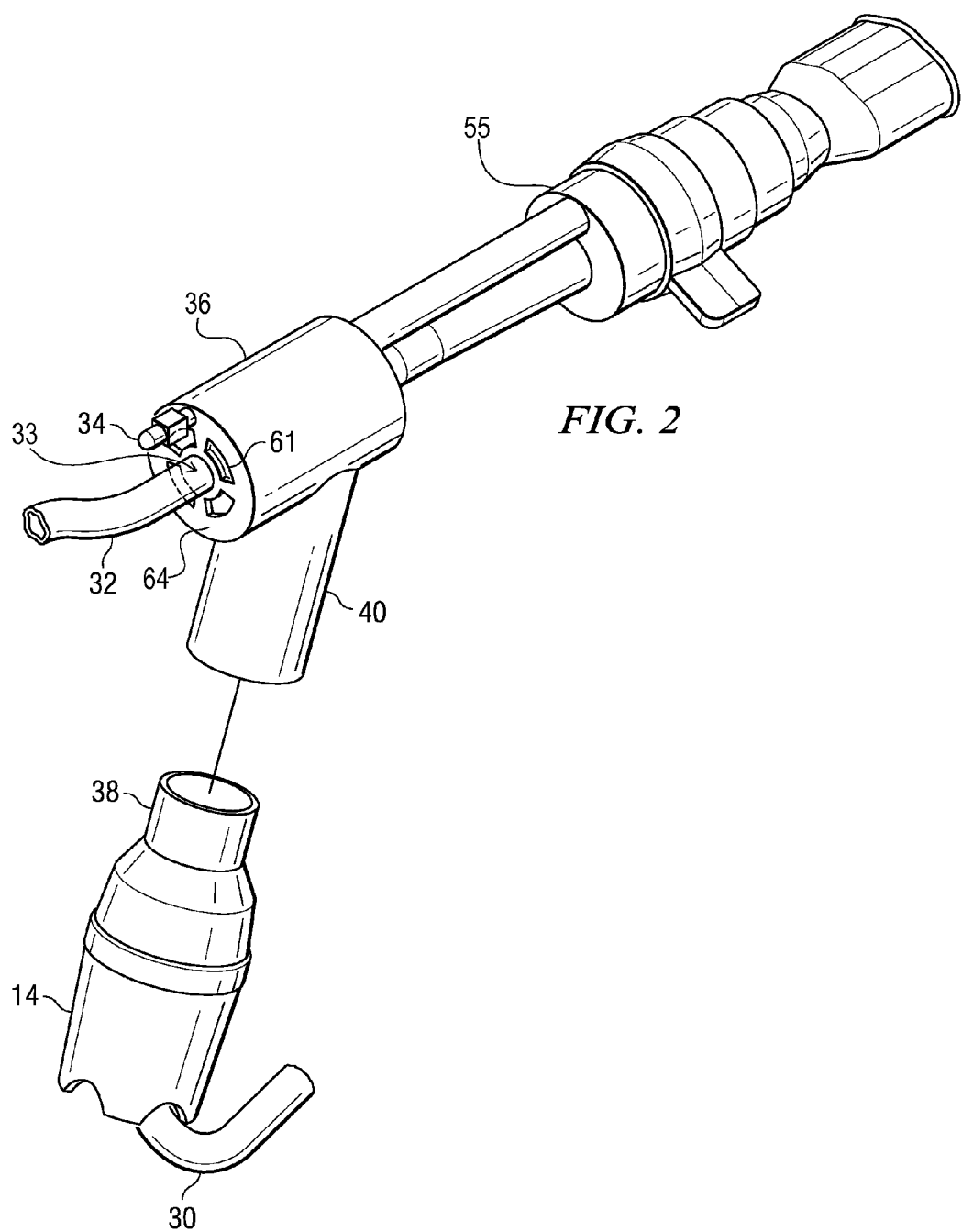
FIG. 2 is a rear view of a preferred embodiment of the lung therapy device of present invention.

FIG. 1 shows an embodiment of the present invention wherein a combination CPAP-aerosol therapy device 10 is formed by attaching a small-volume nebulizer 14 to a single-patient-use CPAP housing 12. Combination CPAP-aerosol therapy device 10 connects to a single gas source (not shown) with single-source gas connector 16.

To initiate the CPAP-aerosol therapy liquid medication is first placed into small-volume nebulizer 14, which is connected to CPAP housing 12 by press fitting nebulizer neck 38 into aerosol port 40. Single-source gas connector 16 is connected to a flow meter (not shown) to regulate the flow of an appropriate source of gas, typically air or oxygen. A manometer (not shown) may be connected to pressure monitoring port 34 in order to adjust the flow meter to achieve the desired pressure. Pressure monitoring port 34 is connected to the distal end of pressure monitoring conduit 42, which is fluidly connected to the proximal end chamber 55 of CPAP housing 12 in order to sense pressure proximal to the patient.

When the combination CPAP-aerosol device 10 has been readied for the therapy mouthpiece 56, which may also be a mask or some other appropriate patient interface, connects the patient to combination CPAP-aerosol device 10 and the patient is instructed to inhale from and exhale into the device.

Flow proceeds from single gas single-source gas connector 16 through singular tube 18 and is divided into two distinct flow streams as it enters Y connector 20. Y connector 20 connects to dual tubing 28, which consists of two tubes: nebulizer tube 58 and CPAP tube 60. From Y connector 20 one of the two flow stream enters into nebulizer tube $1^{st}$ end 22, and the other flow stream enters CPAP tube $1^{st}$ end 24.

The gas flowing through CPAP tube 60 continues until it exits CPAP tube 2nd end 32 and enters into the distal end chamber 36 (also referred to as entrainment cavity 36) of CPAP housing 12. Gas enters into distal end chamber 36 through gas inlet port 33 located in the circular end wall 64 of the distal end chamber 36. The gas flow travels through entrainment cavity 36 and is directed into venturi throat 44. In this embodiment CPAP device 12 contains a venturi 46 which serves as a flow amplification chamber. In alternate embodiments the venturi may be replaced by an amplification chamber which facilitates a Coanda effect, known within the medical industry, which similarly serves as a flow amplification chamber.

Gas flow continues through venturi 46 into proximal end chamber 55 and exits CPAP housing 12 through patient opening 54 and flows into the patient via mouthpiece 56. As the patient exhales, gas may exit exhalation port 62 which is made larger or smaller manipulating exhalation port selector ring 50. By observing manometer pressure exhalation port selector ring 50 may be used to achieve various CPAP pressures in conjunction with varying the flow of the single source gas with a flow meter. The manipulation of exhalation port selector ring 50 is achieved by adjusting exhalation port selector ring tab 52 so that it corresponds with one of three raised indicator dots 48. At one dot the exhalation port is open the most, thereby resulting in the lowest exhalation resistance. At dot three the exhalation port is open the least, thereby resulting in more resistance during exhalation. Accordingly, the housing may include a visual indicator and/or a tactile indicator for indicating the selected size of the exhalation port.

The gas flowing through nebulizer tube 58 is partially restricted by flow reduction orifice 26, which is calibrated in order to regulate the gas to a flow appropriate to drive nebulizer 14. Typically the appropriate flow ranges from 5 to 10 liters per minute. After the gas has passed through flow reduction orifice 26 it continues flowing through nebulizer tube 58 until exits nebulizer tube 2nd end 30, which is connected to nebulizer 14. The gas enters nebulizer 14 where it is utilized to convert the liquid medicine into aerosol. The aerosolized medication flows from nebulizer 14 through nebulizer neck 38 and is entrained into entrainment cavity 36 by way of aerosol port 40.

FIG. 2 depicts a rear view of Combination CPAP-aerosol therapy device 10 showing at least one entrainment opening 61 located in the circular end wall 64 of the distal end chamber 36 through which ambient gas enters into entrainment cavity 36 and mixes with aerosol from nebulizer 14. From there the gas-aerosol mixture enters venturi throat 44, where it travels through venturi 46 and finally out through mouthpiece 56.

What is claimed:

1. A lung therapy device for delivering continuous positive airway pressure, the lung therapy device comprising:

a gas connector to receive a continuous positive flow of gas;

a means for dividing said continuous positive flow of gas into two distinct continuous positive flow streams;

a means for restricting the continuous positive flow of at least one of said two distinct continuous positive flow streams;

a housing fluidly connected to at least one of said two distinct continuous positive flow streams and comprising a proximal end chamber located at a proximal end of said housing and a distal end chamber located at a distal end of said housing;

said housing being devoid of valves that move during the therapy;

said proximal end chamber having a patient opening which therethrough a patient may inhale inspiratory gas into said patient's airways and exhale expiratory gas from said patient's airways;

said patient opening in said proximal end chamber further being fluidly connectable to a patient interface connector;

said distal end chamber comprises:

a substantially flat, substantially circular end wall which is substantially perpendicular to the axial dimension of the housing, a gas inlet port located in said substantially flat, substantially circular end wall and fluidly connectable to one of said two distinct continuous positive flow streams, and a plurality of entrainment ports open to ambient air, wherein the plurality of entrainment ports are located in said substantially flat, substantially circular end wall and arranged so that all ambient air entering the distal end chamber through the plurality of entrainment ports enters the distal end chamber substantially parallel with an axial dimension of the housing defined between the proximal end and the distal end of the housing;

said housing further having a pressure monitoring port located at said distal end, said pressure monitoring port being substantially parallel with the axial dimension;

said housing further containing an amplification chamber connecting said proximal end chamber to said distal end chamber which is shaped such that the flow of gas passing therethrough is amplified;

said housing further containing a port connectable to a nebulizer; and a means for connecting said nebulizer to at least one of said two distinct continuous positive flow streams.

2. The apparatus according to claim 1, wherein said proximal end chamber of said housing further includes at least one exhalation port open to the ambient.

3. The apparatus according to claim 2, wherein said housing further contains a means for adjusting the size of said at least one exhalation port.

4. The apparatus according to claim 3, wherein said means for adjusting said size of said at least one exhalation port is configured to divert the flow of exhaled gas away from a clinician.

5. The apparatus according to claim 3, wherein said housing further comprises a visual indicator, wherein said visual indicator indicates the selected size of said at least one exhalation port.

6. The apparatus according to claim 3, wherein said housing further comprises a tactile indicator, wherein said tactile indicator indicates the selected size of said at least one exhalation port.

7. The apparatus according to claim 1, comprising a pressure monitoring conduit removably connected to said housing having a first end fluidly connected to said proximal end chamber of said housing, and a second end fluidly connected to one end of said pressure monitoring port.

8. The apparatus according to claim 1, wherein said amplification chamber for amplifying said flow of gas within said housing is shaped to form a venturi.

9. The apparatus according to claim 1, wherein said amplification chamber for amplifying said flow of gas within said housing is shaped to create a Coanda effect.

10. A lung therapy device for delivering continuous positive airway pressure, the lung therapy device comprising:
   a gas connector to receive a continuous positive flow of gas;
   a means for dividing said continuous positive flow of gas into two distinct continuous positive flow streams;
   a means for restricting the continuous positive flow of at least one of said two distinct flow streams;
   a housing fluidly connected to at least one of said two distinct continuous positive flow streams and comprising a proximal end chamber located at a proximal end of said housing and a distal end chamber located at a distal end of said housing;
   said housing being devoid of valves that move during the therapy;
   said proximal end chamber having a patient opening which therethrough a patient may inhale inspiratory gas into said patient's airways and exhale expiratory gas from said patient's airways;
   said patient opening in said proximal end chamber further being fluidly connectable to a patient interface connector;
   said proximal end chamber of said housing further including at least one exhalation port open to the ambient air;
   said distal end chamber comprises:
      a substantially flat, substantially circular end wall which is substantially perpendicular to the axial dimension of the housing,
      a gas inlet port located in said substantially flat, substantially circular end wall and fluidly connectable to one of said two distinct continuous positive flow streams, and
      a plurality of entrainment ports open to the ambient, wherein the plurality of entrainment ports are located in said substantially flat, substantially circular end wall and arranged so that all ambient air entering the distal end chamber through the plurality of entrainment ports enters the distal end chamber substantially parallel with an axial dimension of the housing defined between the proximal end and the distal end of the housing;
   said housing further having a pressure monitoring port located at said distal end, said pressure monitoring port being substantially parallel with the axial dimension;
   said housing further containing an amplification chamber connecting said proximal end chamber to said distal end chamber which is shaped to form a venturi such that the flow of gas passing therethrough is amplified;
   said housing further containing a port connectable to a nebulizer;
   a means for connecting said nebulizer to at least one of said two distinct continuous positive flow streams.

11. The apparatus according to claim 10, wherein said housing further contains a means for adjusting the size of said at least one exhalation port.

12. The apparatus according to claim 11, wherein said means for adjusting said size of said at least one exhalation port is configured to divert the flow of exhaled gas away from a clinician.

13. The apparatus according to claim 12, wherein said housing further comprises a visual indicator, wherein said visual indicator indicates the selected size of said at least one exhalation port.

14. The apparatus according to claim 12, wherein said housing further comprises a tactile indicator, wherein said tactile indicator indicates the selected size of said at least one exhalation port.

15. The apparatus according to claim 10, comprising a pressure monitoring conduit removably connected in said housing having a first end fluidly connected to said proximal end chamber of said housing, and a second end fluidly connected to one end of said pressure monitoring port.

16. The apparatus according to claim 10, wherein said amplification chamber for amplifying said flow of gas within said housing is shaped to create a Coanda effect.

* * * * *